United States Patent [19]

Nakagawa et al.

[11] Patent Number: 5,065,625
[45] Date of Patent: Nov. 19, 1991

[54] HUMIDITY METER

[75] Inventors: Shiro Nakagawa; Taisuke Domon; Takehiro Imai, all of Chiba; Atsuko Tsuchida, Saitama, all of Japan

[73] Assignee: TDK Corporation, Tokyo, Japan

[21] Appl. No.: 517,937

[22] Filed: May 2, 1990

[30] Foreign Application Priority Data

| May 12, 1989 | [JP] | Japan | 1-54782 |
| May 15, 1989 | [JP] | Japan | 1-120925 |
| May 15, 1989 | [JP] | Japan | 1-120926 |
| Oct. 9, 1989 | [JP] | Japan | 1-263703 |
| Oct. 11, 1989 | [JP] | Japan | 1-264654 |

[51] Int. Cl.$^5$ .............................................. G01W 1/00
[52] U.S. Cl. .................. 73/336.5; 73/29.02; 73/29.05
[58] Field of Search ............... 338/35; 73/336.5, 29.02, 73/29.05; 324/707, 694; 340/602

[56] References Cited

U.S. PATENT DOCUMENTS

| 4,326,414 | 4/1982 | Terada et al. | 73/336.5 |
| 4,373,392 | 2/1983 | Hagamoto | 73/336.5 |
| 4,646,066 | 2/1987 | Baughman et al. | 73/336.5 |
| 4,649,736 | 3/1987 | Austin | 338/35 |
| 4,816,748 | 3/1989 | Tazawa et al. | 73/336.5 |

FOREIGN PATENT DOCUMENTS

| 123098 | 9/1979 | Japan . |
| 43346 | 3/1984 | Japan . |
| 202051 | 11/1984 | Japan . |
| 76657 | 5/1985 | Japan . |
| 217751 | 9/1986 | Japan . |
| 17649 | 1/1987 | Japan . |
| 108257 | 5/1988 | Japan . |

Primary Examiner—Tom Noland
Assistant Examiner—W. Francos
Attorney, Agent, or Firm—Martin M. Novack

[57] ABSTRACT

A humidity meter includes a humidity-frequency converter which is essentially a pulse oscillator, the frequency of which depends upon the impedance of a humidity sensor, a pulse width modulator for adjusting pulse width of an output pulse of the converter for assuring a linear relationship between humidity and the output signal, and an integrator for integrating the output of the pulse width modulator to provide an output signal as a DC level. A feedback path is provided to apply the output signal to the pulse width modulator for assuring a linear output irrespective of the exponential characteristics of the humidity sensor.

17 Claims, 13 Drawing Sheets

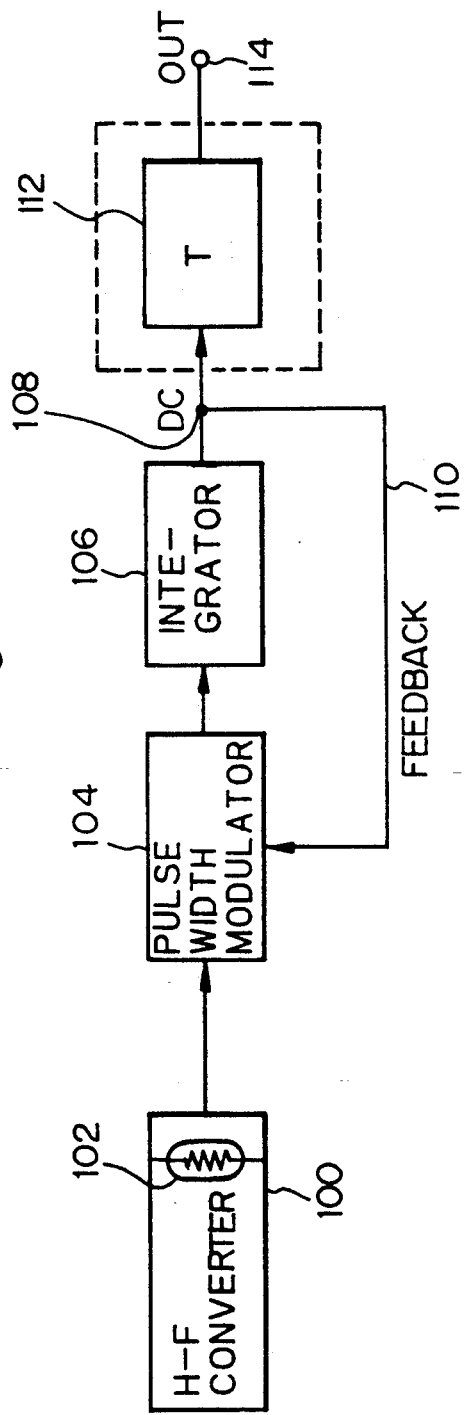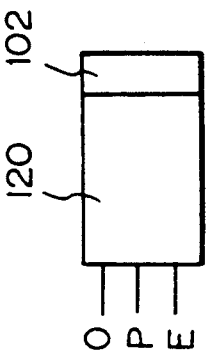

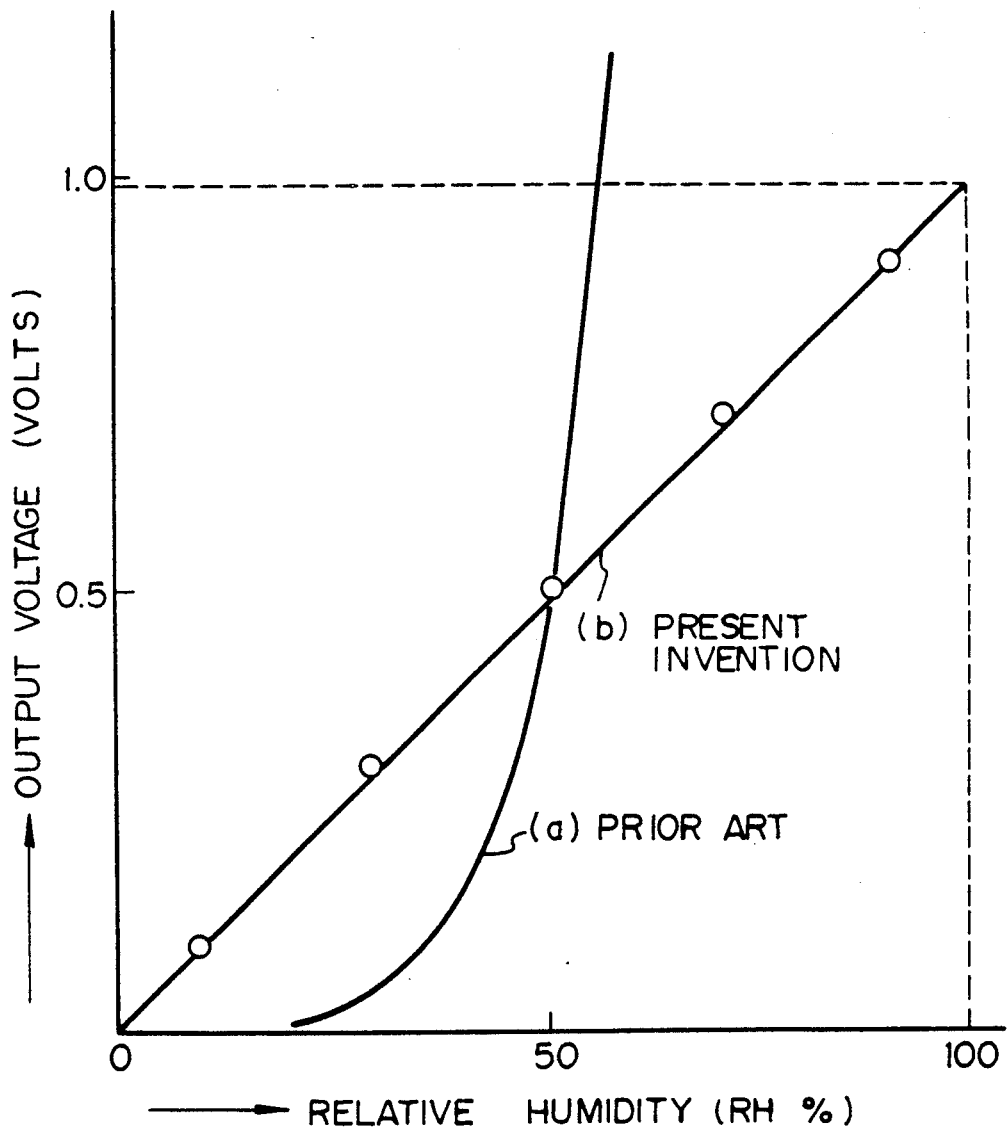

5,065,625

HUMIDITY METER

BACKGROUND OF THE INVENTION

The present invention relates to a humidity meter or a hygrometer which provides DC potential proportional to the measured relative humidity, in particular, relates to such a meter which has a linear relationship between the relative humidity and the output DC potential.

The present humidity meter is applicable to various kinds of electronic apparatuses, including a copying machine, a printer et al, and/or other field of application for visually indicating humidity.

Conventionally, a humidity sensor which provides electrical output relating to humidity has been known. One of them is an impedance change type humidity sensor, including a ceramics type humidity sensor and a polymer type humidity sensor. It is supposed that a water molecule couples with porous ceramics or porous polymer, which is ionized and provides electrical conductivity.

Although the impedance of a conventional humidity sensor relates to relative humidity, the relation between the impedance and the humidity is exponential. When the humidity is low, the impedance is very high, and when the humidity is high, the impedance is very low. A prior electronic circuit is not sufficient for following the wide range of change of the impedance of the humidity sensor.

FIG. 15 is a block diagram of a prior humidity meter. In the figure, the numeral 1 is a humidity-frequency converter, 2 is a differentiation circuit, 3 is a waveform shaping circuit, and 4 is an integrator.

The humidity-frequency converter (H-F converter) 1 provides the output pulses, the frequency of which relates to the humidity. The output pulse of the H-F converter 1 is applied to the differentiation circuit 2. The differentiated pulse is applied to the waveform shaping circuit 4, which takes the signal having the level higher than the predetermined threshold level, and waveform-shapes, and provides the rectangular output pulse. The output pulse of the waveform shaping circuit 3 is applied to the integrator 4, which integrates the input pulses and provides DC (direct current) output level, which relates to the frequency of the output of the converter 1 and the pulse width, or the humidity.

It should be noted in FIG. 15 that the differentiation circuit 2, the waveform shaping circuit 3 and the integrator 4 compose a frequency-voltage converter for converting the frequency to the voltage level by counting the number of pulses.

FIG. 16 is a practical circuit diagram of the prior humidity meter as described in FIG. 15. The same numerals in FIG. 16 show the same members as those in FIG. 16. The symbols $G_1$ through $G_3$ are a gate, $R_1$ through $R_5$ are a resistor, $C_1$ through $C_4$ are a capacitor, and HS is a humidity sensor which changes the impedance depending upon humidity.

The humidity-frequency converter 1 has a C-MOS gate IC (integrated circuit) with a gate $G_2$ (buffer gate) and a gate $G_3$ (inverter), the capacitor $C_1$ and the resistors $R_1$ and $R_2$. Those elements compose an astable multi-vibrator type oscillator.

The series circuit of the humidity sensor HS, the resistor $R_3$ and the capacitor $C_2$ is coupled parallel with the resistor $R_2$ of said oscillator for controlling the oscillation frequency depending upon the humidity. The resistor $R_1$ functions to protect the gate $G_2$. The resistor $R_2$ and the capacitor $C_1$ determine the oscillation frequency. The capacitor $C_2$ functions to prevent DC component applied to the humidity sensor HS. The resistor $R_3$ functions to improve the characteristics of the humidity sensor HS in a high humidity region.

The oscillation frequency of the converter 1 is determined by the capacitor $C_1$, the resistor $R_2$ and the humidity sensor HS. When the humidity around the sensor HS changes, the impedance of the humidity sensor HS follows that change, and then, the oscillation frequency follows the change of the humidity. In other words, the pulse frequency of the oscillator 1 follows the humidity. The output of the oscillator 1 is differentiated by the differentiation circuit 2, which has the capacitor $C_3$ and the resistor $R_4$. The differentiated pulse is waveshaped by the waveform shaping circuit 3 which has the gate $G_1$. The waveform shaped signal is integrated by the integrator 4 which has the resistor $R_5$ and the capacitor $C_4$. The integrated signal is the output which indicates the humidity.

However, a prior humidity meter has the following disadvantages.

1) The change of impedance for humidity is exponential. When humidity is low, impedance is very high, and when humidity is high, impedance decreases substantially. As the impedance changes in very wide range, the frequency change is also very large. For instance, the impedance changes from $10^4$ ohms to $10^7$ ohms. The circuit cannot follow that wide range of frequency, and cannot provide the linear output of humidity.

2) If the time constant of the differential circuit is designed for low humidity (low frequency), the circuit would saturate in high humidity, and the linearity of the circuit would be deteriorated. If the differentiation circuit is designed for high humidity, the output level for low humidity would be too low, and the linearity of the circuit would also be deteriorated.

Further, even if the differentiation circuit is designed for middle humidity, the circuit would not follow low humidity and high humidity, and the problem is not solved.

Therefore, the prior circuit can not follow the wide range of change of impedance of a humidity sensor.

SUMMARY OF THE INVENTION

It is an object of the present invention to overcome the disadvantages and limitations of a prior humidity meter by providing a new and improved humidity meter.

It is also an object of the present invention to provide a humidity meter which can provide a linear output signal depending upon measured humidity in a wide range of humidity.

The above and other objects are attained by a humidity meter comprising; a humidity sensor (102) which provides impedance depending upon humidity to be measured; a humidity-frequency converter (100) for providing an alternate signal of frequency which depends upon the impedance of said humidity sensor (102); a pulse width modulator (104) coupled with output of said humidity-frequency converter (100) for controlling pulse width of said alternate signal; an integrator (106) coupled with output of said pulse width modulator (104) for providing DC potential proportional to frequency and pulse width of output of said pulse width modulator (104); an output terminal (108) coupled with output of said integrator (106) providing measured humidity; a feedback path (110) for providing potential at said output terminal (108) to said pulse width modulator (104) for adjusting pulse width of said alternate signal.

BRIEF DESCRIPTION OF THE DRAWINGS

The foregoing and other objects, features, and attendant advantages of the invention will be appreciated as the same become better understood by means of the following description and accompanying drawings wherein;

FIG. 1A is a block diagram of a humidity meter according to the present invention, FIG. 1B is a plane view of the humidity meter according to the present invention, FIG. 9 shows the characteristics curve of the present humidity meter.

DESCRIPTION OF THE PREFERRED EMBODIMENTS

Figure 2A:
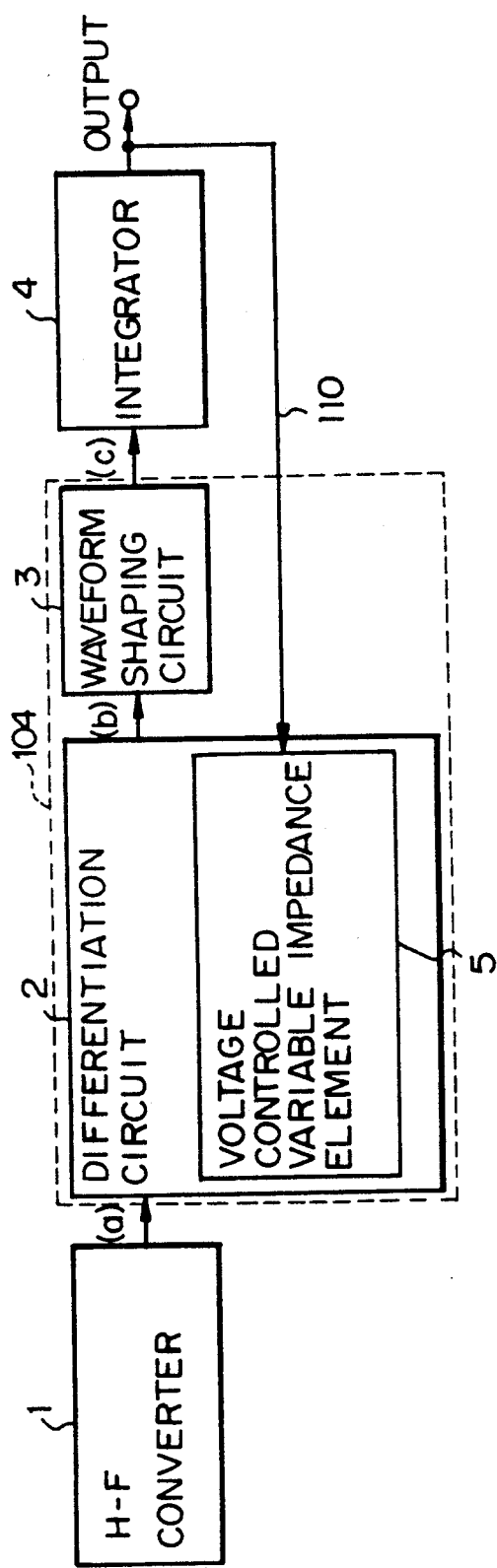
FIG. 2A is a block diagram of the first embodiment of the humidity meter according to the present invention.

FIG. 1 shows a general block diagram of the humidity meter according to the present invention. In the figure, the numeral 100 is H-F (humidity-frequency) converter having a humidity sensor 102. The humidity sensor 102 is, for instance, a high polymer type humidity sensor which changes impedance depending upon humidity. The impedance of the sensor 102 changes exponentially when the humidity changes. The H-F converter 100 provides the frequency output signal. The frequency of the output signal depends upon the impedance of the sensor, or the humidity.

The output of the H-F converter 100 is applied to the pulse width modulator 104, which compensates for the exponential characteristics of the sensor and provides the linear output signal for the humidity. The pulse width modulator 104 is, for instance, composed of a combination of a differentiation circuit with adjustable time constant and a waveform shaping circuit with fixed threshold level, or a combination of a differentiation circuit with fixed time constant and a waveform shaping circuit with adjustable threshold level. The time constant or the threshold level of that pulse width modulator 104 is adjusted by the feedback loop 110 which feedbacks the output signal 108 of the measured humidity. The numeral 106 is an integrator for providing DC (direct current) output level proportional to the measured humidity by integrating the frequency signal.

The output 108 of the integrator 106 may be the final output of the measured humidity, and the output level at the point 108 is applied to the pulse width modulator 104 as a feedback signal.

Preferably, a temperature compensation circuit 112 is coupled with the output 108 so that the temperature dependency of the measured humidity is compensated for, and the output 114 is the final measured humidity.

The humidity sensor 102 is excited with AC (alternate current) signal, since if it is excited with DC signal, the sensor would be undesirably polarized. Further, it is preferable that the sensor is not heated by the exciting power. The converter 100 is essentially an oscillator in which the oscillation frequency depends upon the impedance of the humidity sensor 102. Since the impedance of the sensor 102 varies exponentially with the humidity, the change of humidity by 10 % changes the impedance of the sensor by even 100~500 %. Also, the change of the temperature of the sensor by 0.1° C. would cause the error of the humidity by several %.

The pulse width modulator 104, which is implemented by a differentiation circuit or a waveform shaping circuit compensates the exponential relationships, and provides the linear output signal relating to the humidity. The time constant of the differentiation circuit or the threshold level of the waveform shaping circuit is adjusted by the feedback circuit 110 which takes an output signal 108. The integrator 106 provides the DC signal level which is proportional to the humidity, and the output 108 of the integrator 106 is fedback to the pulse width modulator 104. The DC level indicating the humidity is subject to the temperature compensation by the circuit 112, and the final humidity output level is obtained at the output of the temperature compensation circuit 112.

FIG. 1B shows the plan view of the present humidity meter, which is mounted on a printed circuit board 120 of the size for instance 10 mm x 26 mm x 5 mm. The humidity sensor 102 is coupled with said printed circuit board. The printed circuit board has three pins 0, P and E for external connection. The pin 0 is an output terminal. The pin P is power supply terminal for the electrical circuit, and the pin E is a ground terminal.

Therefore, it should be appreciated that the present humidity meter is very small in size, and the wire for connecting the meter to the humidity meter may be long. It should be noted further that the humidity sensor 102 is directly coupled with the printed circuit board 120. The direct coupling is advantageous since the impedance of the sensor 102 is high when the humidity is low, and the long wire of the sensor 102 would cause the measurement error of the humidity.

FIG. 2A is a block diagram of the first embodiment of the present humidity meter. In the figure, the numeral 1 is a H-F converter which is the same as 100 in FIG. 1A, the numeral 2 is a differentiation circuit having a voltage controlled variable impedance element 5 for adjusting the time constant of the differentiation. The numeral 3 is a waveform shaping circuit having the fixed threshold level, and 4 is an integrator. The integrator 4 provides the DC output level corresponding to the frequency and the pulse width of the input signal.

Figure 2B:
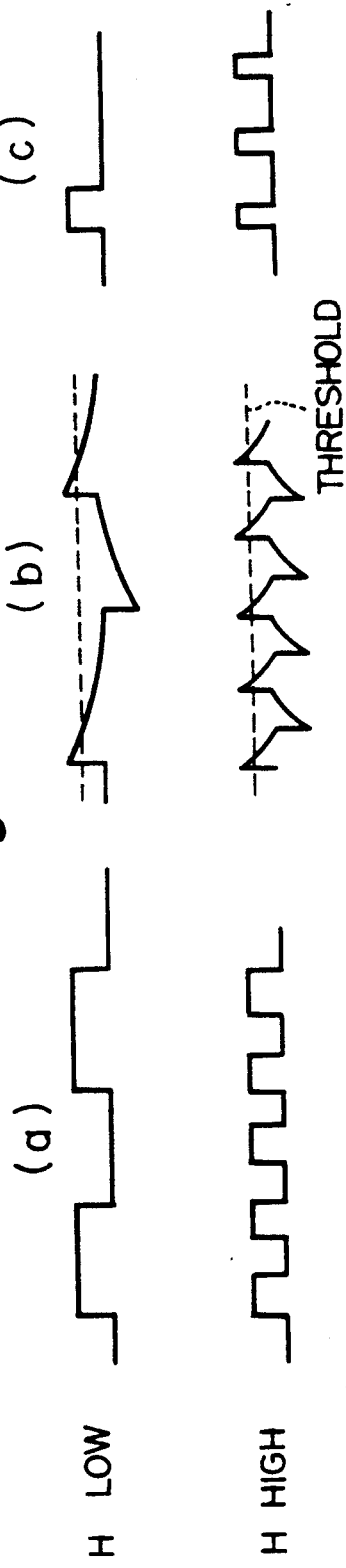
FIG. 2B shows operational waveforms of the apparatus of FIG. 2A.

FIG. 2B shows the operational waveforms at the points (a), (b) and (c) in FIG. 2A. When the humidity is low, the frequency is low, and when the humidity is high, the oscillation frequency is high as shown in FIG. 2B(a).

The output of the H-F converter 1 is applied to the differentiation circuit 2. The time constant of that differentiation circuit 2 is large when the output humidity level is low, and is small when the output humidity level is high as shown in FIG. 2B(b). The waveform shaping circuit 3 shapes the waveform of the output of the differentiation circuit 2 with the predetermined threshold level. That is to say, the waveform shaping circuit 3 provides an output pulse with the pulse width which is equal to the duration that the input signal to the waveform shaping circuit 3 exceeds the predetermined threshold level. The output of the waveform shaping circuit 3 is shown in FIG. 2B(c). It should be noted that when the humidity is low, the frequency is low and the pulse width is wide, and when the humidity is high, the frequency is high and the pulse width is narrow. The output of the waveform shaping circuit 3 is applied to the integrator 4, which provides the DC output level which is proportional to the area of the pulse signal shown in FIG. 2B(c).

The output DC level of the integrator 4 is fedback to the differentiation circuit 2 so that the time constant of that circuit is adjusted by changing the impedance of the variable impedance element in that differentiation circuit 2.

FIGS. 3 through 8 show the practical circuit diagram which embodies the block diagram of FIG. 2A. In those figures, the symbol $T_r$ is a transistor, $R_6$ through $R_{11}$ are a resistor, $C_5$ through $C_9$ are a capacitor, D is a diode, VD is a variable capacitance diode, TH is a thermistor, EX-OR is an exclusive-OR circuit, VR is a variable resistor, 6 is a temperature compensation circuit, and $G_4$ is a gate (inverter).

Figure 3:
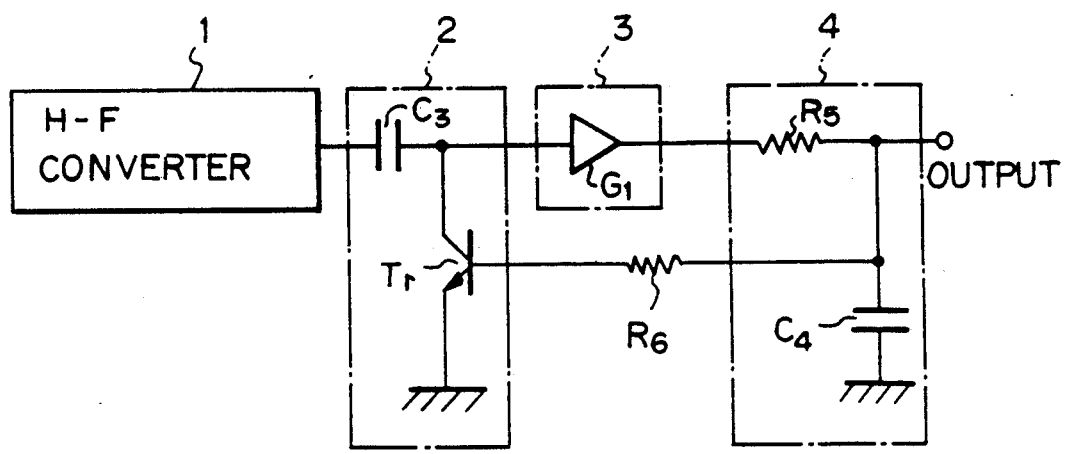
FIG. 3 is a circuit diagram of the humidity meter embodying the block diagram of FIG. 2A.

FIG. 3 is a first circuit diagram, in which the transistor $T_r$ is used as an impedance element of the differentiation circuit 2, which is composed of the capacitor $C_3$ and the transistor $T_r$. The base of the transistor $T_r$ receives the output signal from the output terminal which is the output of the integrator 4 through the resistor $R_6$.

When the output level of the integrator 4 is high (high humidity), the resistance between the collector and the emitter of the transistor $T_r$ is low, and the time constant of the differentiation circuit 2 is small. On the other hand, when the output level of the integrator 4 is low (low humidity), the resistance between the collector and the emitter of the transistor $T_r$ is high, and the time constant of the differentiation circuit 2 is large.

Therefore, the time contant of the differentiation circuit 2 is adjusted according to the humidity, and the exponential characteristics of the humidity sensor are compensated, and the linear relationship between the humidity and the output DC level is obtained.

Figure 4:
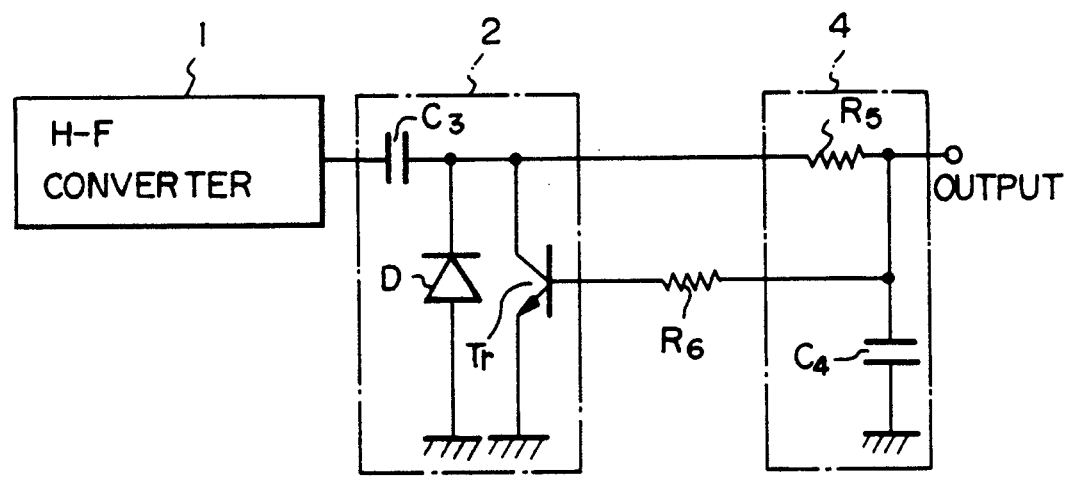
FIG. 4 is another circuit diagram of the humidity meter according to the present invention.

FIG. 4 is a modification of FIG. 3. The feature of FIG. 4 is that the waveform shaping circuit 3 in FIG. 3 is omitted, and a diode D is coupled parallel to the transistor $T_r$.

When no waveform shaping circuit 3 is used, both the positive pulse and the negative pulse from the differentiation circuit 2 would be applied directly to the integrator 4, and no correct humidity output would be obtained. Therefore, a diode D is inserted so that the negative component of the differentiation circuit 2 is grounded and only the positive component of the differentiated pulse is forwarded to the integrator so that the humidity related DC output is obtained at the output of the integrator 4.

Figure 5:
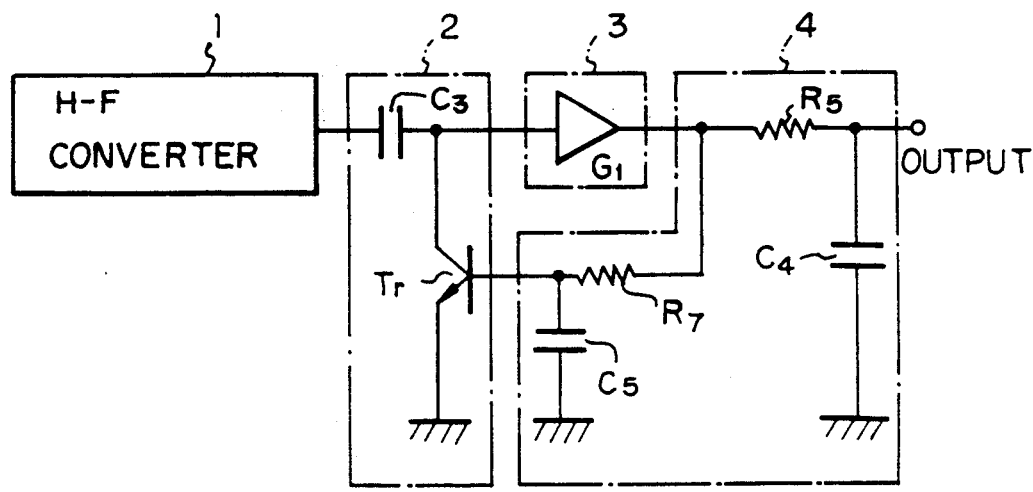
FIG. 5 is still another circuit diagram of the humidity meter according to the present invention.

FIG. 5 is another modification of FIG. 3. The feature of FIG. 5 is that the integration circuit 4 has a pair of integrators ($R_5C_4$) and ($R_7C_5$). The first integrator ($R_5C_4$) is used for the integration of an output signal, and the second integrator ($R_7C_5$) is used for the integration of the feedback signal. Therefore, the time constant of the feedback loop is adjusted independent from the time constant of the output humidity signal.

Figure 6:
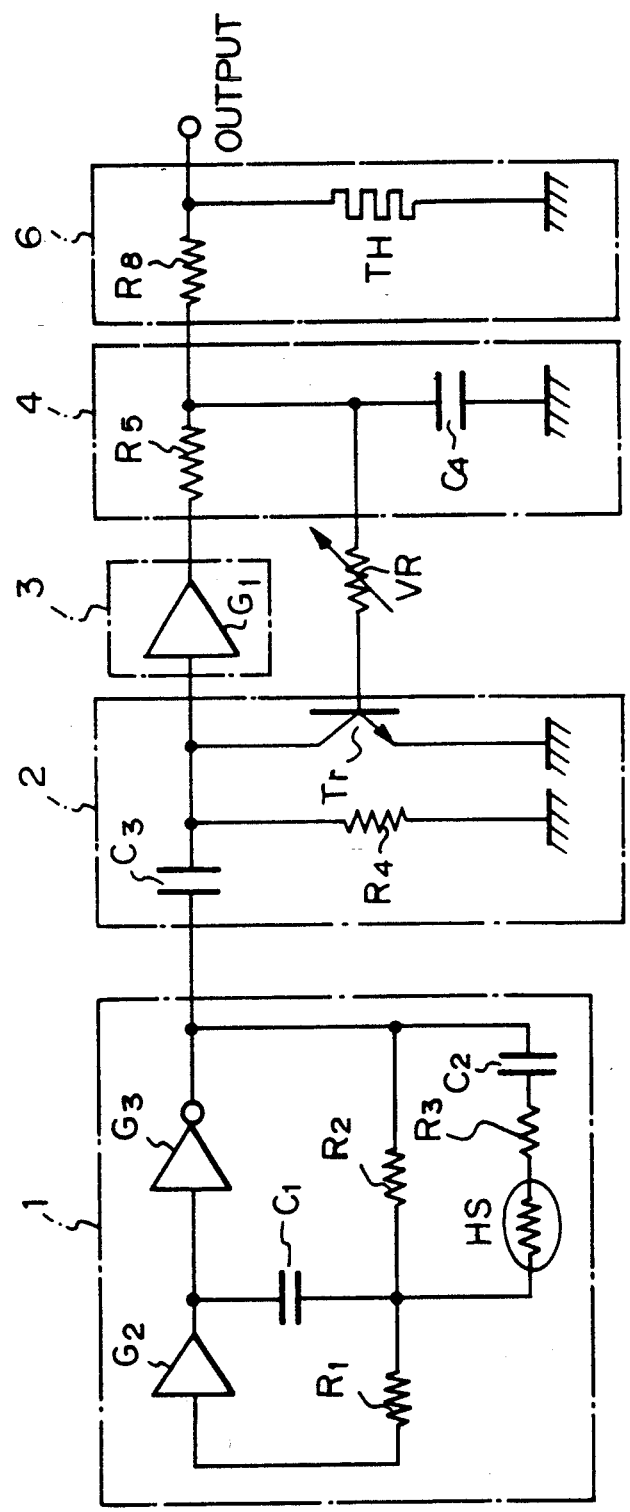
FIG. 6 is still another circuit diagram of the humidity meter according to the present invention.
Figure 16:
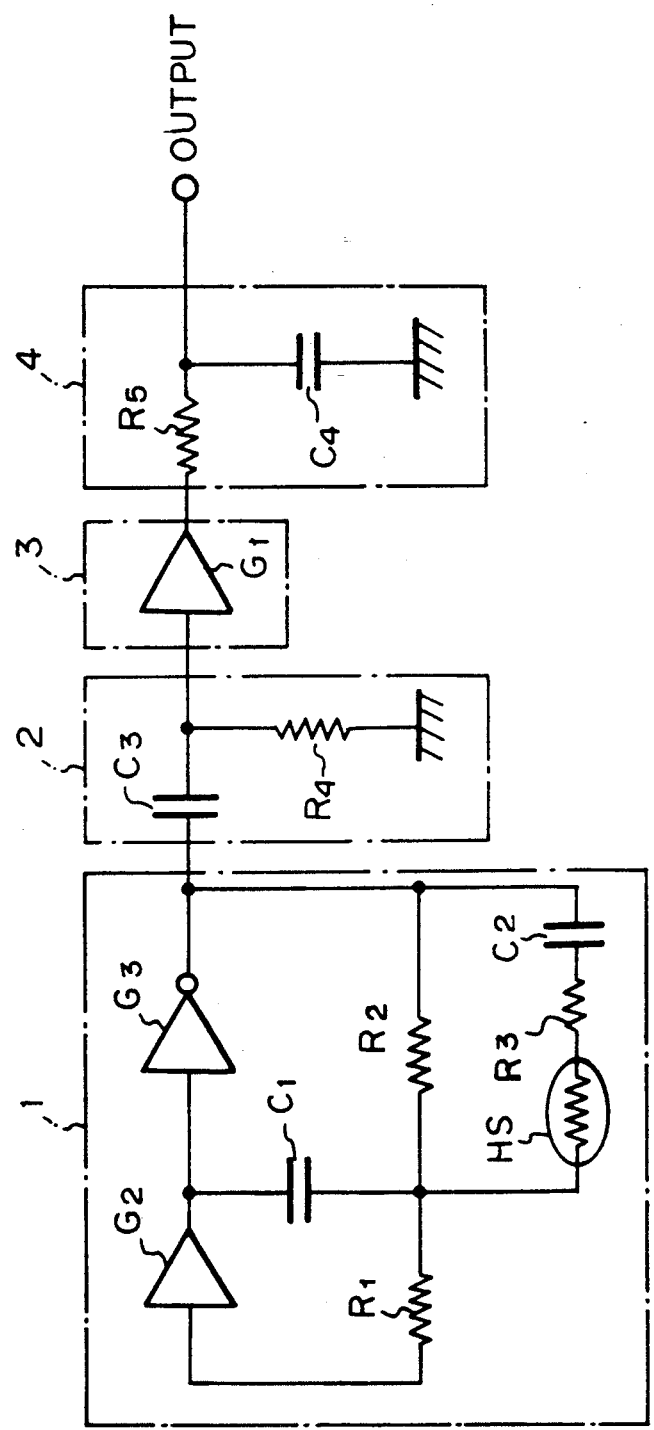
FIG. 16 is a circuit diagram which embodies the prior humidity meter of FIG. 15.

FIG. 6 is still another modification of FIG. 3. The H-F converter 1 in FIG. 6 is the same as that of the prior art FIG. 16. The differentiation circuit 2 in FIG. 6 has a capacitor $C_3$, and the parallel circuit of the resistor $R_4$ and the transistor $T_r$ between the output of the capacitor $C_3$ and the ground. The variable resistor VR is inserted between the base of the transistor $T_r$ and the integrator 4 for adjusting the base current of the transistor $T_r$.

Further, the temperature compensation circuit 6 having the resistor $R_8$ and the thermistor TH between the output terminal and the ground is provided at the output of the integrator 4.

When the humidity is low and the output frequency is low, the output level of the integrator 4 is very low, and therefore, the resistance beween the collector and the emitter of the transistor $T_r$ is extremely high, and no current flows in the collector of the transistor $T_r$. The resistor $R_4$ is coupled parallel with the transistor $T_r$. The resistor $R_4$ functions to keep the operation of the differentiation circuit 2 even when the resistance between the collector and the emitter of the transistor $T_r$ is extremely high, so that the present circuit operates correctly even when the humidity is very low.

The operation of the H-F converter 1 is as follows.

When the power switch (not shown) is put ON, no charge is stored in the capacitor $C_1$, and so, the output of the gate $G_2$ is at a low level (0), and the output of the gate $G_3$ is at a high level (1). Therefore, the current flows from the output of the gate $G_3$ to the input of the gate $G_3$ through the network of ($R_2$, HS, $R_3$, $C_2$, $C_1$). That current charges the capacitor $C_1$, and when the input of the gate $G_3$ reaches the level (1), the output of the gate $G_3$ becomes (0), and the capacitor $C_1$ is charged in the opposite direction. When the level at the junction of the resistor $R_1$ and the resistor $R_2$ decreases to the predetermined level, the input of the gate $G_2$ becomes (0), and the output of that gate $G_2$ becomes also zero. That is to say, the input of the gate $G_3$ becomes (0). The above operation is repeated.

As the charge current and the discharge current of the capacitor $C_1$ flows in the humidity sensor HS, the oscillation frequency of the converter 1 depends upon the impedance of the humidity sensor HS.

Figure 7:
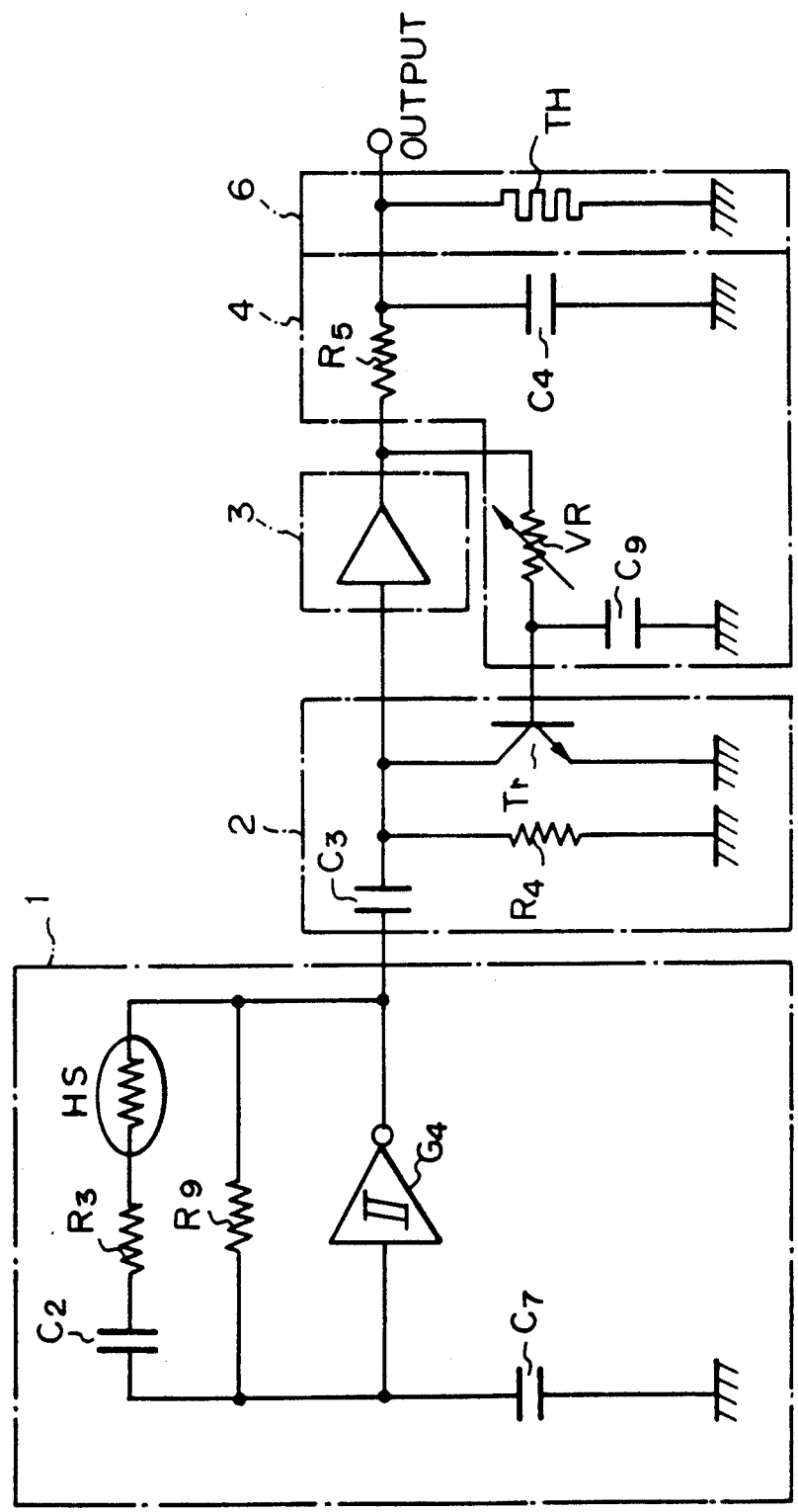
FIG. 7 is still another circuit diagram of the humidity meter according to the present invention.

FIG. 7 is still another modification of FIG. 3. In this modification, the H-F converter 1 is implemented by an astable multivibrator which has a gate $G_4$ (inverter), a capacitor $C_7$, and a resistor $R_9$. The series circuit of the humidity sensor HS, the resistor $R_3$ and the capacitor $C_2$ is coupled parallel with the resistor $R_9$. The capacitor $C_2$ functions to prevent DC potential applied to the humidity sensor HS.

Supposing that the output of the gate $G_4$ is at high level (1), the capacitor $C_7$ is charged through the resistor $R_9$, and the potential across the capacitor $C_7$ increases gradually. When the potential across the capacitor $C_7$ exceeds the threshold level of the gate $G_4$ of the Schmitt trigger circuit (astable multivibrator), the gate $G_4$ inverts, and the output of the gate $G_4$ becomes to low level (0). Then, the capacitor $C_7$ discharges through the resistor $R_9$, and the potential across the capacitor $C_7$ decreases. When the potential across the capacitor $C_7$ decreases to the second threshold level (lower threshold level), the output of the gate $G_4$ becomes to high level (1) again. The above operation is repeated, and the astable multivibrator circuit (Schmitt trigger circuit) oscillates.

As the humidity sensor HS is coupled parallel with the resistor $R_9$ through the capacitor $C_2$ and the resistor $R_3$, the combined resistance of the parallel circuit depends upon the resistance of the humidity sensor HS, and the impedance of the humidity sensor HS can adjust the oscillation frequency.

The structure of the differentiation circuit 2 is the same as that of FIG. 6. The integration circuit 4 has a first integrator with the resistor $R_5$ and the capacitor $C_4$, and the second integrator with the variable resistor VR and the capacitor $C_9$. The temperature compensation circuit 6 is coupled with the output of the integration circuit 4.

The H-F converter 1 in FIG. 7 has the advantage as compared with that of FIG. 6, that only one gate is enough for oscillation, and the potential change of the input of the gate is smaller than that of FIG. 6. Therefore, the power consumption is smaller than that of FIG. 6, and therefore, the heat generation is also smaller.

Figure 8:
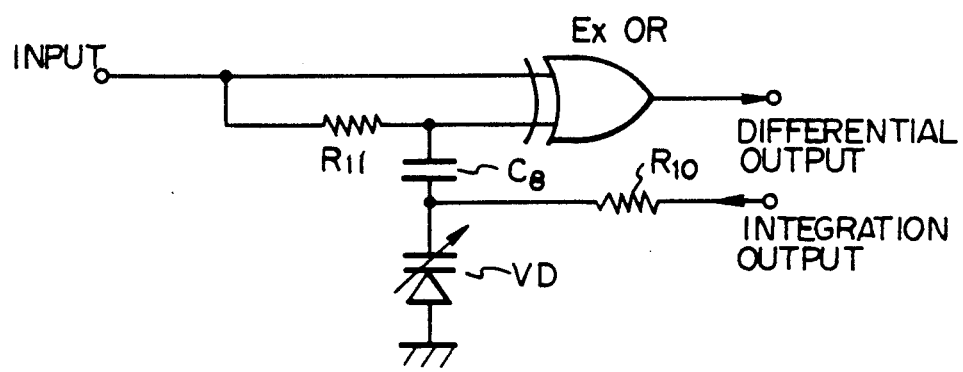
FIG. 8 is a circuit diagram of a differentiation circuit.

FIG. 8 shows the modification of a differentiation circuit, in which an input signal is applied to one input of an exclusive-OR circuit (EX-OR), and simultaneously, the input signal is applied to the integration circuit with the resistor $R_{11}$ and the capacitor $C_8$ and the variable capacitance diode VD. The output of said integration circuit is applied to another input of said exclusive-OR circuit. The capacitance of the variable capacitance diode VD is controlled by the output potential of the integration circuit 4.

In operation, when the input signal is (0), both the inputs of the exclusive-OR circuit are (0), and the output of the exclusive-OR circuit is (0). When the input signal changes to (1), the first input of the exclusive-OR circuit changes to (1) quickly and the second input of the exclusive-OR circuit changes to (1) after the integration circuit ($R_{11}$, $C_8$, VD) provides an output signal. Therefore, the output signal of the exclusive-0R circuit when an input signal changes to (1) is first (1), and then, changes to (0). Therefore, it should be appreciated that the circuit of FIG. 8 having an exclusive-OR circuit and an integration circuit functions essentially as a differentiation circuit.

The differentiation circuit of FIG. 8 can be used in any embodiments described above.

FIG. 9 shows the characteristics curves of the present humidity meter in an experiment. The horizontal axis in FIG. 9 shows the relative humidity in %, and the vertical axis shows the output voltage of the humidity meter (FIGS. 3 through 7). The curve (a) in FIG. 9 shows the prior humidity meter of FIG. 16, in which it should be noted that the output signal is very low for the low humidity, and the output voltage is high for high humidity, and further, the relations between the humidity and the output signal are not linear but exponential.

On the other hand, the present humidity meter has the linear characteristics between the humidity and the output signal as shown in the curve (b) in FIG. 9, and the wide range from 0 % to 100 % of humidity.

Some modifications are possible to those skilled in the art. For instance, a voltage controlled variable impedance element is not restricted to a bipolar transistor as shown in FIG. 3, but the use of an FET is possible. As for a H-F converter, the circuit is not restricted to that of FIG. 3 or FIG. 7, but any oscillator which depends the oscillation frequency to the impedance of the humidity sensor is possible. The present invention is applicable to a temperature meter by replacing a humidity sensor to a temperature sensor (for instance a thermistor). Further, the relations to the output signal and the humidity may be reverse so that the output signal is higher when the humidity is lower, merely by inversing the output signal by an inverter.

Figure 10A:
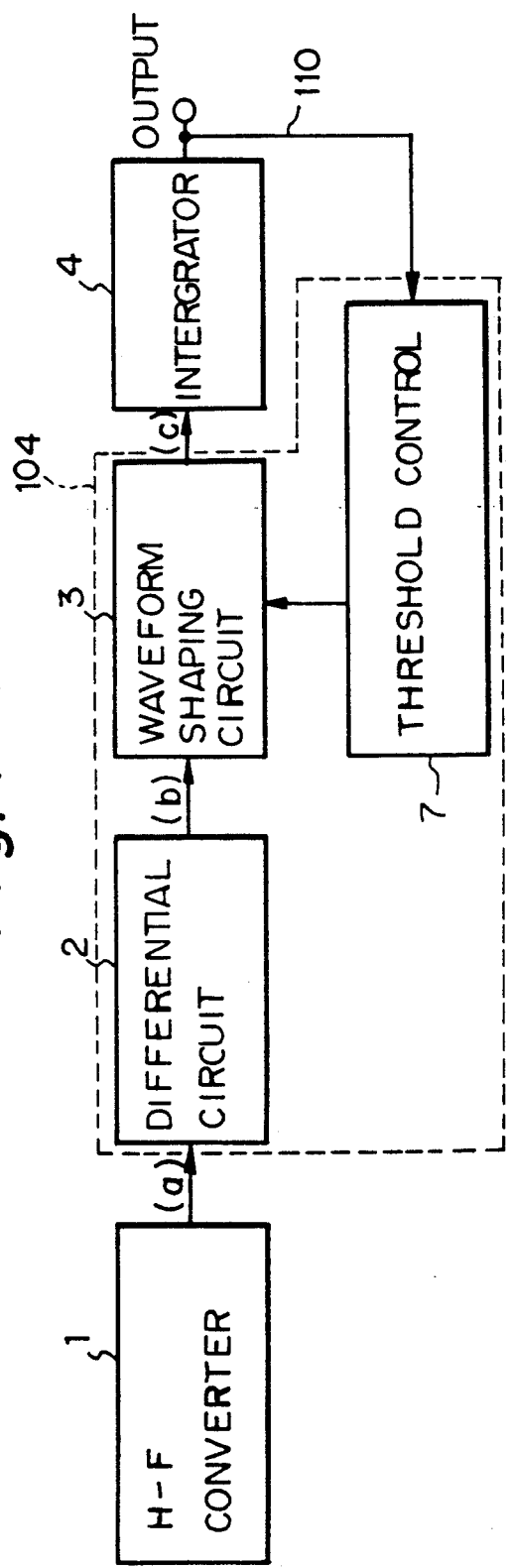
FIG. 10A is a block diagram of the second embodiment of the humidity meter according to the present invention.
Figure 10B:
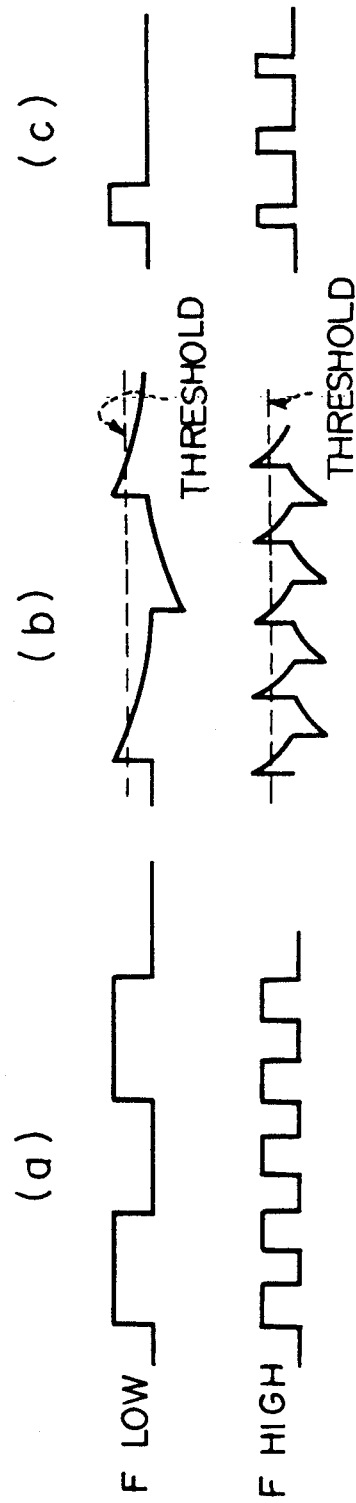
FIG. 10B shows operational waveforms of the apparatus of FIG. 10A.

FIG. 10A is a block diagram of the second embodiment of the present humidity meter for implementing the general idea of FIG. 1A. In FIG. 10A, the H-F converter 1 and the integrator 4 are the same as those in FIG. 2A. The pulse width modulation circuit in FIG. 10A comprises a fixed differentiation circuit 2 with fixed time constant, and a waveform shaping circuit 3 which has a variable threshold level by a variable threshold control 7. The threshold control 7 is coupled with the output of the integrator 4 so that the threshold level of the waveform shaping circuit 3 is high when the output of the integrator 4 is high, and the threshold level is low when the output of integrator 4 is low. FIG. 10B shows the operational waveforms at the points (a), (b) and (c) in FIG. 10A. The output (a) of the H-F converter 1 is low frequency signal or high frequency signal depending upon the humidity is low or high as shown in FIG. 10B(a). The rectangular pulse signal at the output of the converter 1 is differentiated by the differentiation circuit 2 which has the fixed time constant. The waveforms at the point (b) of the output of the differentiation circuit 2 are shown in FIG. 10B(b), in which each pulse signal has decreasing slope as shown in the figure.

The waveform shaping circuit 3 shapes the waveforms of FIG. 10B(b) so that the pulse portion which exceed the predetermined threshold level is shaped to rectangular pulse form. Therefore, when the threshold level is high, the pulse width of the shaped pulse is narrow, and when the threshold level is low, the pulse width of the shaped pulse is wide.

The waveform (c) shows the output of the waveform shaping circuit 3, and it should be noted that the pulse width is modulated depending upon the output DC level. The shaped pulse signal is applied to the integrator 4, which integrates the pulse signal to provide the DC output signal which represents the measured humidity. The output of the integrator 4 is fedback to the threshold control 7 to adjust the threshold level according to the output level of the integrator 4. FIGS. 11 through 14 show the practical circuit diagram which embodies the block diagram of FIG. 10A. In those figures, the symbol $T_r$ shows a transistor, $R_6$ through $R_{12}$ are a resistor, TH is a thermistor, OP is an operational amplifier, G4 is a gate (inverter), and $C_5$ is a capacitor.

Figure 11:
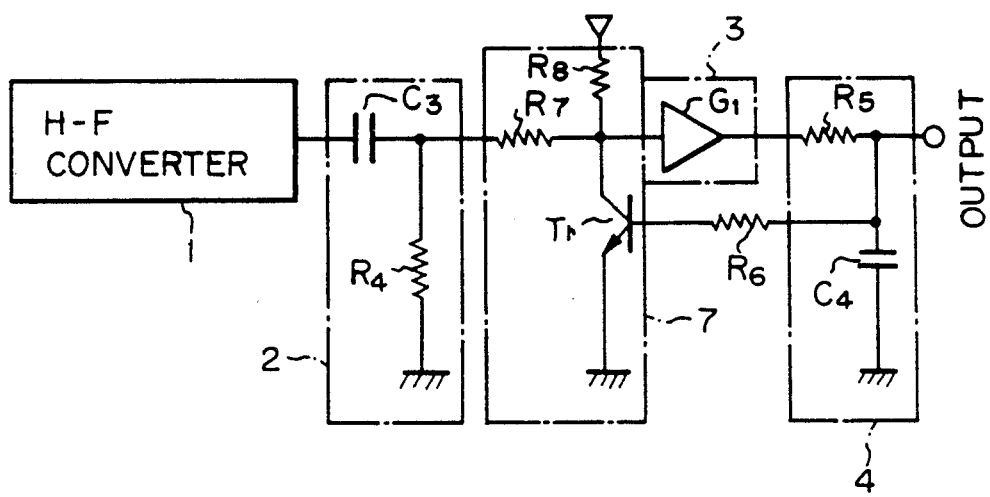
FIG. 11 is a circuit diagram which embodies the block diagram of FIG. 10A.

FIG. 11 is a first circuit diagram which embodies the block diagram of FIG. 10A. In FIG. 11, the waveform shaping circuit 3 is implemented by a gate $G_1$ (buffer gate), and the threshold control 7 is comprised of a transistor $T_r$, and the resistors $R_7$ and $R_8$. The base of the transistor $T_r$ is coupled with the output of the integrator 4 through the resistor $R_6$ which restricts the base current. The resistor $R_7$ is coupled between the output of the differentiation circuit 2 and the input of the waveform shaping circuit 3. The resistor $R_8$ is coupled beween the input of the waveform shaping circuit 3 and the predetermined potential.

The integrator 4 is comprised of the resistor $R_5$ and the capacitor $C_4$, and the potential across the capacitor $C_4$ is applied to the base of the transistor $T_r$ through the resistor $R_6$.

As the base current of the transistor $T_r$ varies according to the output potential of the integrator 4, the resistance between the collector and the emitter of the transistor $T_r$ varies also according to the output potential of the integrator 4. Therefore, the potential at the input of the gate $G_1$ changes, in other words, the threshold level of the gate $G_1$ changes.

The threshold level of the waveform shaping circuit 3 is high when the humidity is high, and the threshold level is low when the humidity is low. Thus, the threshold level is adjusted according to the humidity, and the linear output of the measured humidity is obtained.

Figure 12:
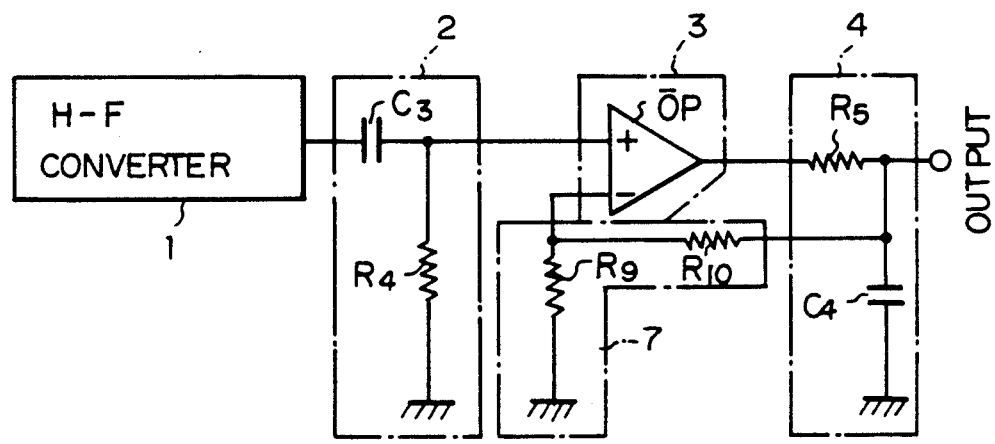
FIG. 12 is another circuit diagram of the humidity meter according to the present invention.

FIG. 12 is a modification of FIG. 11. The feature of FIG. 12 is that the waveform shaping circuit 3 is implemented by an operational amplifier OP, and the threshold control 7 is implemented by a voltage divider coupled with one input of said operational amplifier OP. The voltage divider is comprised of the resistor $R_9$ and the resistor $R_{10}$.

The output of the integrator 4 is divided by the resistors $R_9$ and $R_{10}$, and the divided voltage is applied to one input of the operational amplifier OP. The output of the differentiation circuit 2 is applied to the other input (+) of the operational amplifier OP, and the operational amplifier OP provides an output pulse when the input signal to the input terminal (+) is higher than the input signal at the terminal (−) which accepts the threshold level. Thus, the waveform shaping circuit 3 provides an output signal only when an input signal exceeds a threshold level.

Figure 13:
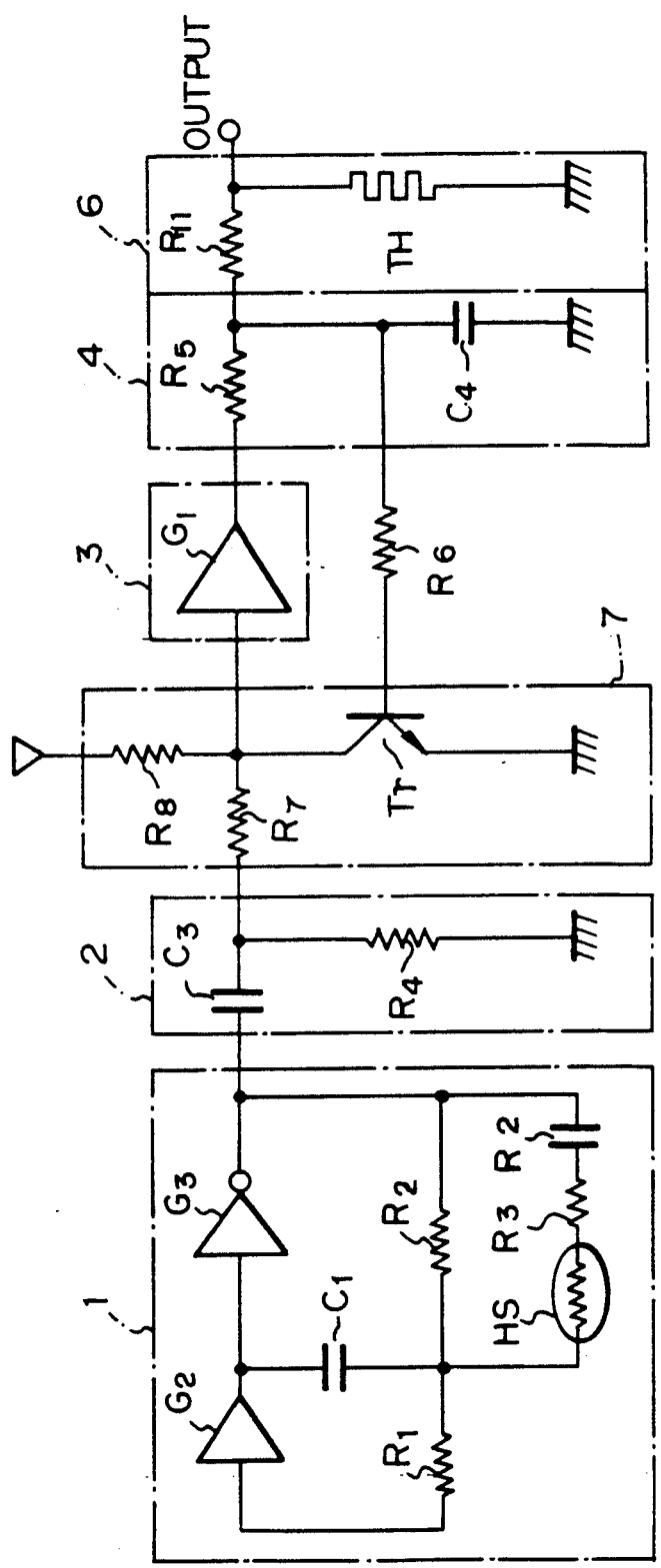
FIG. 13 is still another circuit diagram of the humidity meter according to the present invention.

FIG. 13 shows a circuit diagram of still another modification of FIG. 10A. The H-F converter 1 in FIG. 13 is the same as that of FIG. 6. The differentiation circuit 2, the threshold control 7, the waveform shaping circuit 3 and the integrator 4 in FIG. 13 are the same as those in FIG. 11. FIG. 13 has the temeperature compensation circuit 6 which has the resistor $R_{11}$ and the thermistor TH across the output terminal and the ground for compensating the output voltage drift because of the temperature change. The temperature compensation circuit 6 is the same as that of FIG. 6 in structure.

Figure 14:
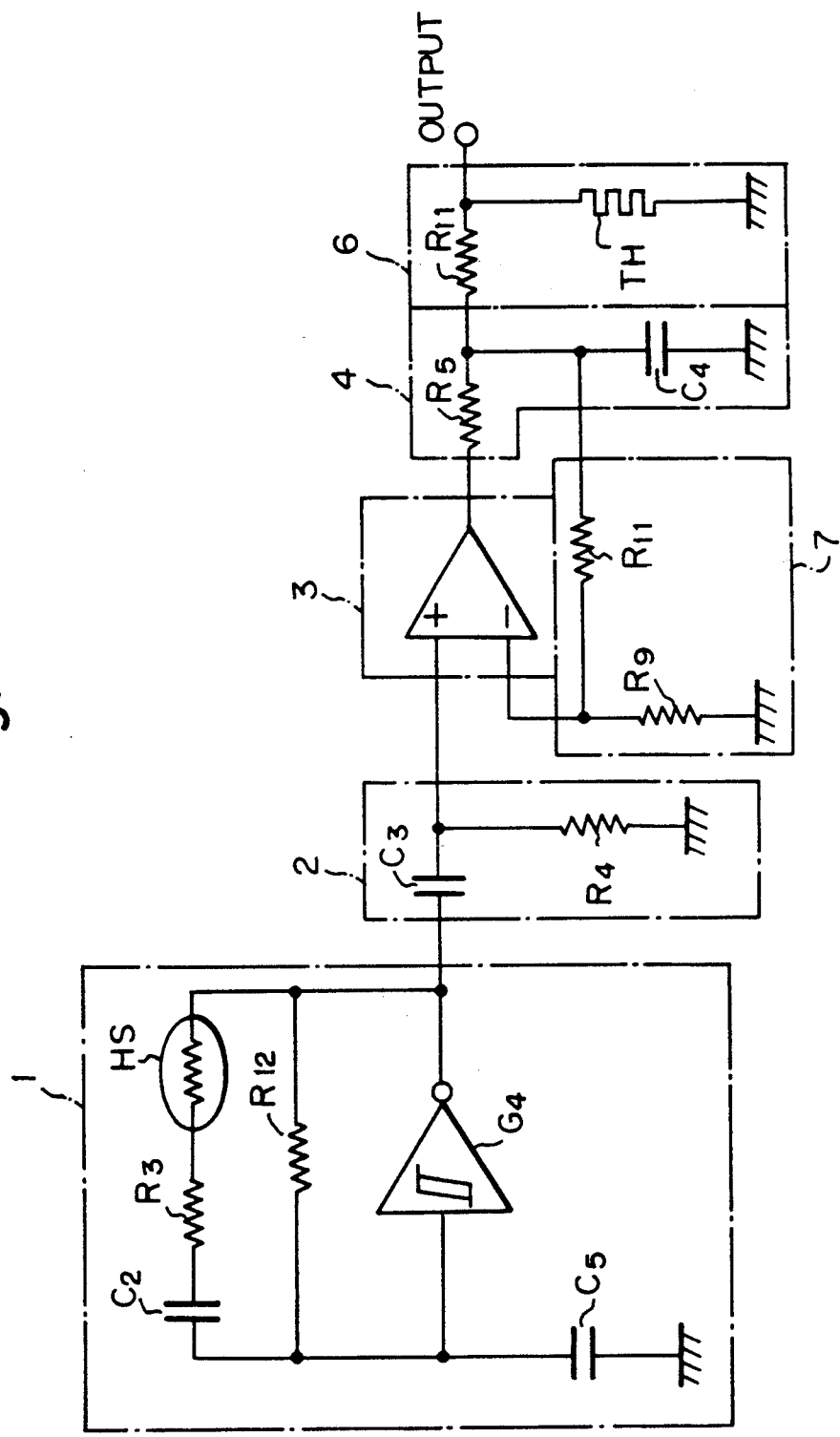
FIG. 14 is still another circuit diagram of the humidity meter according to the present invention.
Figure 15:
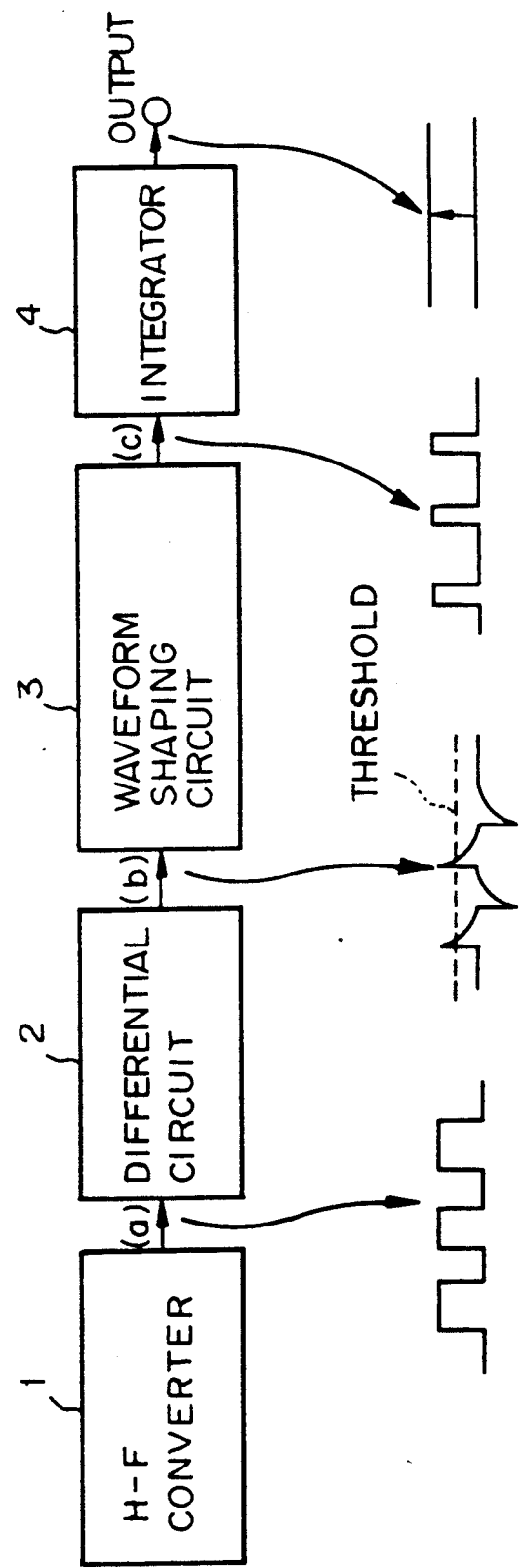
FIG. 15 is a block diagram of a prior humidity meter.

FIG. 14 shows a circuit diagram of still another modification of the FIG. 10A. The H-F converter 1 in FIG. 14 is the same as that of FIG. 7. The differentiation circuit 2, the waveform shaping circuit 3, the integrator 4 and the threshold control 7 in FIG. 14 are the same as those in FIG. 12. FIG. 14 has the temperature compensation circuit 6 at the output of the integrator 4. The structure of the temperature compensation circuit 6 is the same as that of FIG. 13.

The second embodiment in FIGS. 10A through 14 has the linear characteristics as shown in FIG. 9 (curve (b)), as is the case of the first embodiment.

The modifications are of course possible in the second embodiment to those skilled in the art. For instance, a transistor in a threshold control is not restricted to a bipolar transistor, but an FET is possible. Also, a temperature meter is also possible merely by replacing a humidity sensor to a temperature sensor (for instance a thermistor).

As described above in detail, according to the present invention, the linear relations between the humidity and the measured output potential are obtained. Since the electronic circuit is simple and small in size, it is possible to mount both the electronic circuit and a sensor in a small housing as shown in FIG. 1B, and therefore, the total size of the humidity meter is small, and further, since the humidity sensor is connected to the electronic circuit with very short lead wire, no error occurs because of the impedance of a lead wire.

From the foregoing it will now be apparent that a new and improved humidity meter has been found. It should be understood of course that the embodiments disclosed are merely illustrative and are not intended to limit the scope of the invention. Reference should be made to the appended claims, therefore, rather than the specification as indicating the scope of the invention.

What is claimed is:

1. A humidity meter comprising;
    a humidity sensor (102) which provides impedance depending upon humidity to be measured,
    a humidity-frequency converter (100) for providing an alternate signal of frequency which depends upon the impedance of said humidity sensor (102),
    a pulse width modulator (104) coupled with output of said humidity-frequency converter (100) for controlling pulse width of said alternate signal,
    an integrator (106) coupled with output of said pulse width modulator (104) for providing potential proportional to frequency and pulse width of output of said pulse width modulator (104),
    an output terminal (108) coupled with output of said integrator (106) providing measured humidity,
    a feedback path (110) for providing potential at said output terminal (108) to said pulse width modulator (104) for adjusting pulse width of said alternate signal.

2. A humidity meter according to claim 1, wherein a temperature compensation circuit (112) is provided at output of said integrator (106).

3. A humidity meter according to claim 1, wherein said humidity-frequency converter (100), said pulse width modulator (104), said integrator (106) and said feedback path (110) are mounted on a single common printed circuit board (120), which is coupled directly with said humidity sensor (102), and said printed circuit board (120) has three pins for external connection for output of the measured humidity, power supply, and ground.

4. A humidity meter according to claim 1, wherein said pulse width modulator (104) comprises a differentiation circuit (2) and means (5) for adjusting time constant of said differentiation circuit (2) according to feedback signal through said feedback path (110).

5. A humidity meter according to claim 4, wherein said differentiation circuit (2) is comprised of a capacitor ($C_3$) coupled with output of said humidity-frequency converter (100), and a transistor ($T_r$) with collector coupled with output of said capacitor ($C_3$), emitter grounded, and base coupled with said beedback path (110).

6. A humidity meter according to claim 5, wherein a diode (D) is coupled parallel to said transistor ($T_r$) with polarity opposite to that of the transistor.

7. A humidity meter according to claim 1, wherein said integrator (106) has a first integration circuit ($R_5C_4$) for humidity measurement, and a second integration circuit ($R_7C_6$) in feedback path.

8. A humidity meter according to claim 1, wherein said pulse width modulator (106) comprises an exclusive-OR circuit with first input coupled with output of said humidity-frequency converter (100) and second input coupled with output of said humidity-frequency converter (100) through a resistor ($R_{11}$), a series circuit of a capacitor ($C_8$) and a variable capacitance diode (VD) coupled between said second input of said exclusive-OR circuit and ground, and junction point of said capacitor and said variable capacitance diode being coupled with said feedback path.

9. A humidity meter according to claim 4, wherein a variable resistor (VR) is inserted in said feedback path.

10. A humidity meter according to claim 1, wherein said humidity-frequency converter (100) is essentially an oscillator having a humidity sensor as one of frequency decision elements.

11. A humidity meter according to claim 10, wherein said oscillator comprises a pair of gates ($G_2$, $G_3$), a pair of series connected resistors ($R_1$, $R_2$) coupled between output of one gate ($G_3$) and input of the other gate ($G_2$), a capacitor ($C_1$) coupled between junction of said first gate and said second gate, and junction of said resistors, and a series circuit of a humidity sensor (HS), a resistor ($R_3$) and a capacitor ($C_2$) coupled parallel with said resistor ($R_2$).

12. A humidity meter according to claim 10, wherein said oscillator comprises a gate ($G_4$) with an input grounded through a capacitor ($C_7$), a resistor ($R_9$) coupled between an input and an output of said gate, and a series circuit of a humidity sensor (HS), a resistor ($R_3$) and a capacitor ($C_2$) coupled parallel with said resistor ($R_9$), and a frequency output at output of said gate.

13. A humidity meter according to claim 1, wherein said pulse width modulator (104) comprises a differentiation circuit with a fixed time constant, a waveform shaping circuit coupled with output of said differentiation circuit for providing a shaped pulse signal when level of output of said differentiation circuit exceed a predetermined threshold level, and a threshold control (7) coupled with said feedback path (110) for adjusting said threshold level.

14. A humidity meter according to claim 13, wherein said waveform shaping circuit is a gate, and said threshold control has a voltage divider with a pair of resistors ($R_7$, $R_8$), and a transistor for adjusting resistance of one of said resistors.

15. A humidity meter according to claim 13, wherein said waveform shaping circuit has an operational amplifier with a first input coupled with output said differentiation circuit, and a second input coupled with output of said integrator through a voltage divider ($R_9$, $R_{10}$).

16. A humidity meter according to claim 2, wherein said temperature compensation circuit (112) comprises a resistor ($R_8$) with one end coupled with output of said integrator (106), and a thermistor (TH) coupled between the other end of said resistor ($R_8$) and ground.

17. A humidity meter according to claim 1, wherein said humidity sensor (102) provides capacitance depending upon humidity to be measured.

* * * * *